(12) United States Patent
Nazer et al.

(10) Patent No.: US 12,408,912 B1
(45) Date of Patent: Sep. 9, 2025

(54) SUTURING ASSEMBLY INCLUDING A DOUBLE-HEADED CURVED NEEDLE

(71) Applicant: KING SAUD UNIVERSITY, Riyadh (SA)

(72) Inventors: Rakan Ibrahim Nazer, Riyadh (SA); Ali Mufraih Albaratti, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 19/039,417

(22) Filed: Jan. 28, 2025

(51) Int. Cl.
*A61B 17/06* (2006.01)

(52) U.S. Cl.
CPC ............ *A61B 17/06066* (2013.01); *A61B 2017/06052* (2013.01); *A61B 2017/0609* (2013.01); *A61B 2017/061* (2013.01)

(58) Field of Classification Search
CPC .......... A61B 17/06066; A61B 17/0609; A61B 17/06004; A61B 17/06166; A61B 2017/06171; A61B 2017/06047
See application file for complete search history.

(56) References Cited

U.S. PATENT DOCUMENTS

| | | | | |
|---|---|---|---|---|
| 5,865,836 A * | 2/1999 | Miller | ................... | A61B 17/06 606/228 |
| 5,941,899 A * | 8/1999 | Granger | ............ | A61B 17/06066 606/222 |
| 6,197,043 B1 * | 3/2001 | Davidson | ................ | A61L 17/10 606/228 |
| 7,850,600 B1 | 12/2010 | Piskun | | |
| 2003/0083674 A1 | 5/2003 | Gibbens, III | | |
| 2007/0219586 A1 * | 9/2007 | Mahadevan | ..... | A61B 17/06066 606/224 |
| 2010/0023054 A1 | 1/2010 | Matsutani et al. | | |
| 2010/0263425 A1 | 10/2010 | Matsutani et al. | | |
| 2011/0130773 A1 | 6/2011 | Saliman et al. | | |
| 2012/0109193 A1 * | 5/2012 | Primavera | ........ | A61B 17/06166 606/228 |
| 2015/0032143 A1 * | 1/2015 | Khouri | ................. | A61B 17/205 606/186 |
| 2018/0199936 A1 * | 7/2018 | Kelner | ............. | A61B 17/06166 |
| 2019/0183487 A1 | 6/2019 | Kim | | |

FOREIGN PATENT DOCUMENTS

WO  WO-2010006448 A1 * 1/2010 ............. A01K 91/04

* cited by examiner

Primary Examiner — Tuan V Nguyen
(74) *Attorney, Agent, or Firm* — Nath, Goldberg & Meyer; Joshua B. Goldberg

(57) ABSTRACT

A suturing assembly includes a needle, a suture thread and a flexible member connecting the needle with the suture thread. The needle has a curved body with a sharp tip on either end. The needle includes a cavity that extends throughout the entire length of the needle body, between its two sharp tips. The needle also includes a slit extending along the entire length of the needle body, the slit exposing the cavity of the needle body to the outside of the needle body along the length of the needle body. The suture thread may be surgical grade thread. The flexible member may be made of an elastomeric material that includes silicone. The flexible member may have one end thereof connected to the cavity of the needle body, and the other end thereof connected to the suture thread. The suturing assembly can be used in a method of suturing.

19 Claims, 6 Drawing Sheets

SUTURING ASSEMBLY INCLUDING A DOUBLE-HEADED CURVED NEEDLE

TECHNICAL FIELD

The present disclosure relates to a suturing assembly, and more particularly, to a suturing assembly including a double-headed curved needle.

DISCUSSION OF THE RELATED ART

Surgical needles are well-known in the medical arts. Old forms of surgical needles resemble sewing needles to some degree. That is, the front end of the needle is sharp, the rear end of the needle has an eye, and thread is passed through the eye to connect the thread with the needle. The thread must be reliably fixed to the needle, a process that typically involves tying a knot near the eye of the needle. However, the part of the thread that passes through the eye and/or the knot typically cause a localized "bump" or a localized widening of the needle due to the thread being overlaid on the needle and/or the knot being wider than the diameter of the thread (or widening the needle body).

The localized "bump" increases the size (or diameter) of the piercing that is needed to enable the needle, the thread and the knot to pass through bodily tissue, as compared to the size of a piercing that will enable the needle by itself to pass through tissue. This increase in the size of the piercing increases trauma on the bodily tissue, thereby increasing the healing time and increasing the risk for developing other health complications.

Swaged needles were created to overcome this disadvantage. Swaged needles are needles, used mainly for surgery, that have a body with sharp front end (or front tip), a rear end, and thread that extends from the rear end of the needle body as if it were a continuation of the needle body. Therefore, swaged needles do not have any knots in the thread, and do not have thread overlaid on the needle body. As such, swaged needles avoid creating a larger piercing in bodily tissue than the size of the piercing that is needed to enable the needle by itself to pass through the tissue.

The problem with known swaged needles is that they are unidirectional. That is, only the sharp front tip of the needle can be used to pierce through bodily tissue, with the swaged rear end following from behind to pass the thread through the tissue. This configuration is disadvantageous because it requires a surgeon to rotate the needle in the opposite direction (e.g., turn the needle around to point backwards) after having made a suture. That is, after having passed the needle with the thread through bodily tissue in a given direction (say from left to right), the surgeon must rotate the needle such that the needle can be used to pierce the bodily tissue in the right to left direction (or opposite direction) to create the next suture.

The maneuvering that is required to turn the needle body in the opposite direction is difficult, especially when the working space is limited, such as inside of a bodily cavity (e.g., in the abdominal cavity, the pelvic cavity, etc.) of a patient. This difficulty increases the length of time required to complete the suturing process. In addition, the process of turning the needle around inside of a bodily cavity to create the next suture increases the risk of harming the patient by having the surgeon inadvertently puncture or scratch an unrelated organ with the needle during the turning process.

SUMMARY

The present disclosure relates to a suturing assembly that can be used to overcome the problems associated with conventional and swaged needles, particularly when used in bodily cavities. More specifically, the present subject matter relates to a curved and double-headed needle that overcomes the problem of needing to rotate a conventional/swaged needle after completing a suture while boasting the puncture-reducing feature of swaged needles.

Regarding the elimination of the need to rotate the needle, since the needle of the present disclosure is double headed, the tip of the needle that was at the rear during the last completed suture (e.g., the non-piercing end during the previous suture) will naturally be positioned to face, and therefore to pierce, the bodily tissue for the subsequent suture. For example, when piercing bodily tissue from the left to right direction to form a first suture, the tip of the needle that was at the back of the needle body during the left to right movement can be used as the front tip to pierce the bodily tissue in the right to left direction for creating the subsequent suture, and vice-versa. Therefore, no rotation of the needle of the present subject matter is needed to orient its sharp end toward bodily tissue after having completed a suture since both ends of the needle of the present disclosure are sharp and usable for suturing.

Regarding the puncture-size-reducing feature of the assembly of the present subject matter, the double headed needle taught by this specification has an interior channel (also referred to as a "cavity" in this specification) that runs the entire length of the needle body. The needle body also has a slit that runs the entire length of the needle body. The slit exposes the channel along the entire length of the channel. This configuration enables the suture thread, along with a flexible, thread-like flexible member that connects the suture thread to the needle body inside of the interior channel, to be inserted inside of the channel through the slit. Therefore, the thread-like flexible connecting member and the suture thread can be housed inside of the channel at the time the needle passes through bodily tissue. Therefore, the needle of the present subject matter punctures a hole in bodily tissue that is only as big as it needs to be to allow the needle to pass therethrough. In other words, the puncture hole does not need to be larger than the exterior diameter/width of the needle because the thread passes through the inside of the needle (thus is not overlaid on the outside of the needle), and no knots are used in the present disclosure to tie the thread to the needle.

Notably, the configuration of the assembly of the present disclosure is advantageous because it enables the suture thread to automatically be inserted in the interior channel of the needle while the surgeon is passing the needle through bodily tissue to create a suture. This is because the slit enables access to the interior channel of the needle, while a constriction (or puncture hole) of the bodily tissue (at the interface where the needle punctured the tissue) guides the suture thread toward the slit and into the channel. This applies when suturing from either end of the double-headed needle of the present disclosure.

BRIEF DESCRIPTION OF THE DRAWINGS

The above and other features of the present disclosure will become more apparent by describing in detail exemplary embodiments thereof in conjunction with the accompanying drawings, in which.

DETAILED DESCRIPTION OF THE EMBODIMENTS

Figure 1:
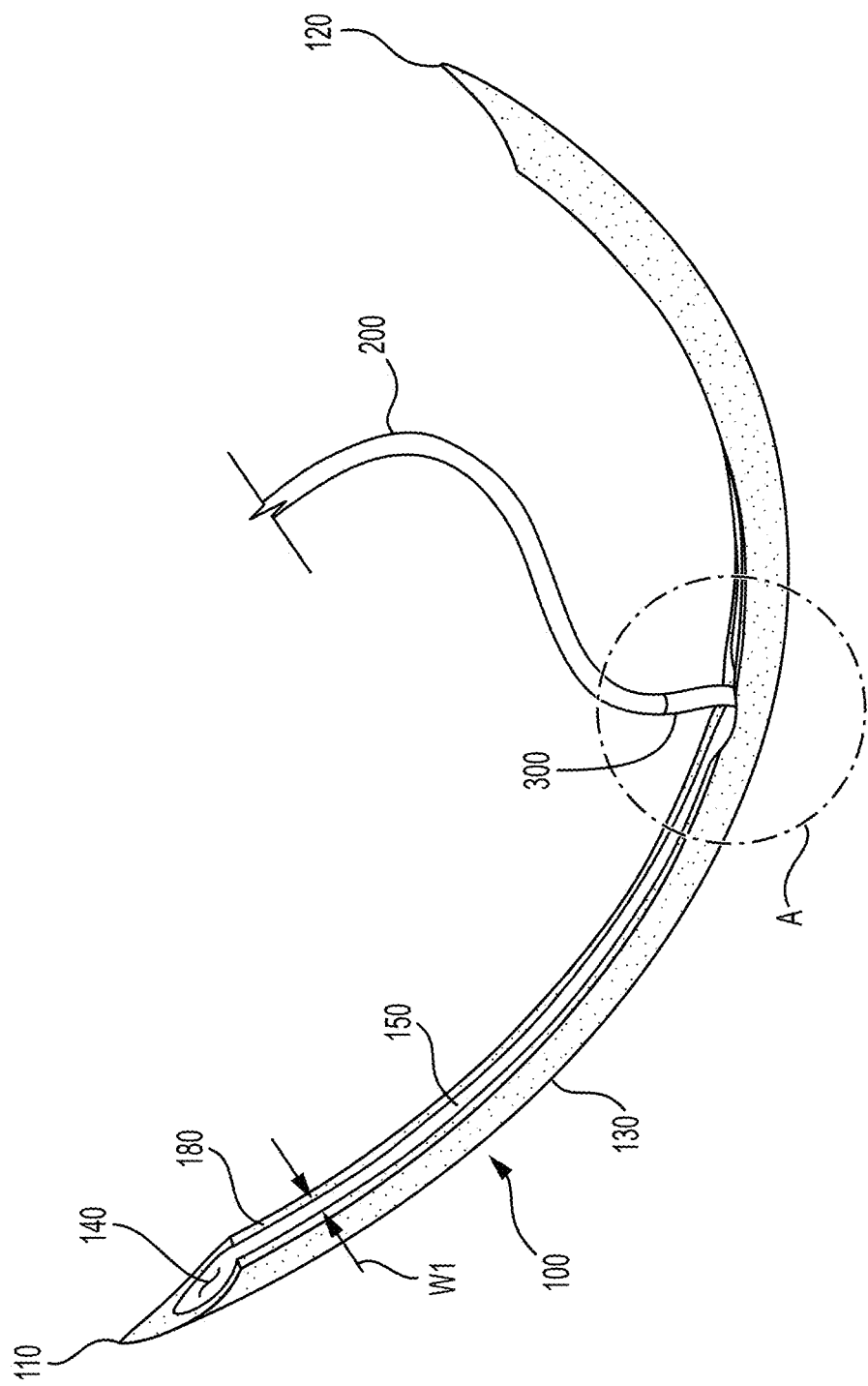
FIG. 1 is a perspective view illustrating a suturing assembly in accordance with an embodiment of the present disclosure.

Exemplary embodiments of the present disclosure will be described more fully hereinafter with reference to the accompanying drawings. The present disclosure may, however, be embodied in different forms and should not be construed as being limited to the embodiments set forth herein. Like reference numerals may refer to like elements throughout the specification. The sizes and/or proportions of the elements illustrated in the drawings may be exaggerated for clarity.

When an element is referred to as being disposed on another element, intervening elements may be disposed therebetween. In addition, elements, elements, components, parts, etc., not described in detail with respect to a certain figure or embodiment may be assumed to be similar to or the same as corresponding elements, components, parts, etc., described in other parts of the specification.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" may include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, size ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Referring to FIGS. 1-10, a suturing assembly may include a needle 100, a suture thread 200, and an elongated flexible member 300 connecting the suture thread 200 and the needle 100 to one another.

The elongated flexible member 300 may be referred to as a "flexible member" 300 for brevity purposes.

The needle 100 may include a first end 110 defining a first tip of the needle 100, a second end 120 defining a second tip of the needle 100, and a needle body 130 extending between the first and second ends 110, 120. The first and second tips of the needle 100 may be sharp to facilitate piercing.

The needle body 130 may be made of a metal or of an alloy of metals. The needle body 130 may comprise, by way of non-limiting example, stainless steel (e.g., surgical grade stainless steel), titanium (e.g., surgical grade titanium), etc.

The needle body 130 includes a cavity 140 that extends throughout the needle body 130, along a length of the needle body 130 between the first and second ends 110, 120. For example, the cavity 140 may extend throughout the entire length of the needle body 130. The cavity 140 is exposed to the outside of the needle body 130 at the first and second ends 110, 120 of the needle body 130.

In addition, the needle body 130 includes a slit 150 extending along the length of the needle body 130, between the first and second ends 110, 120. For example, the slit 150 may extend along the entire length of the needle body 130.

The slit 150 exposes the cavity 140 of the needle body 130 from the outside of the needle body 130, along the length of the needle body 130.

Figure 5:
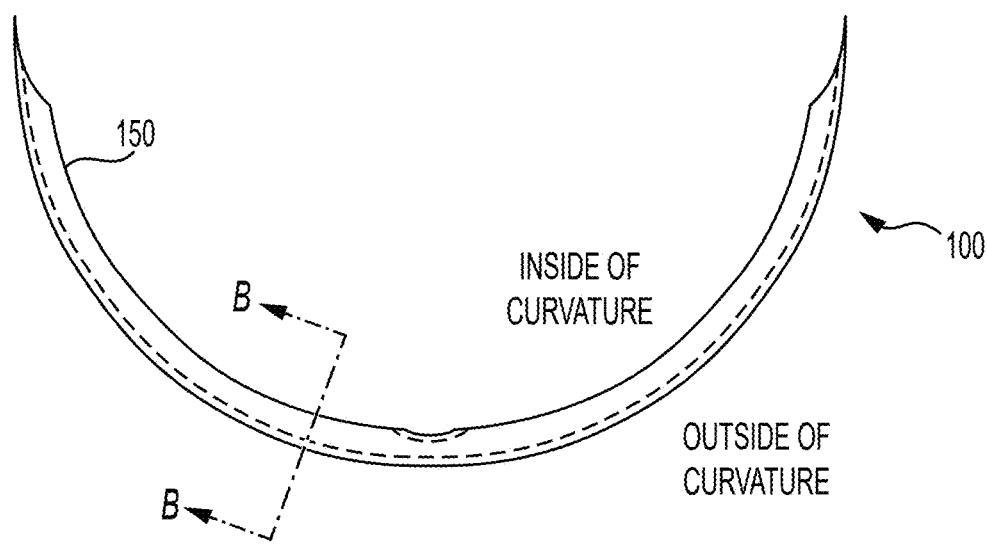
FIG. 5 is a side view illustrating the needle body of the suturing assembly of FIG. 1 in isolation from the flexible member and suture thread.
Figure 6:
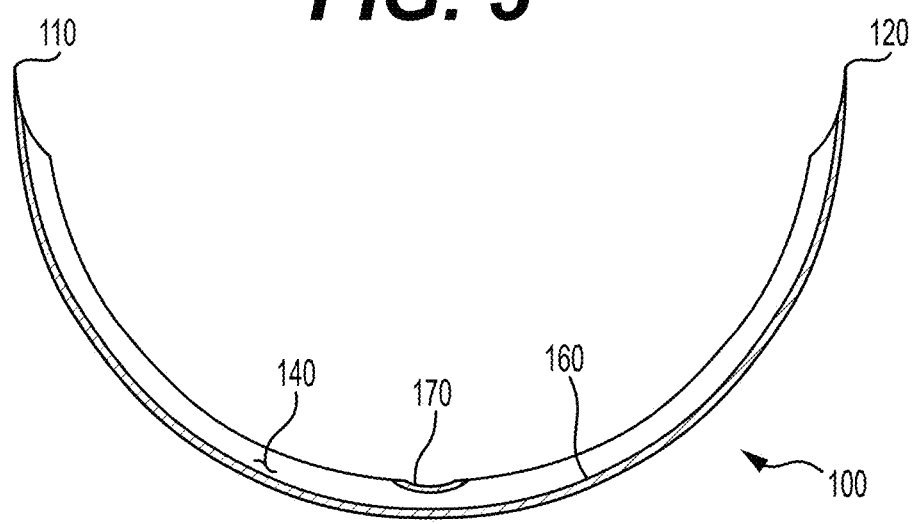
FIG. 6 is a cross-sectional view taken along line A-A of FIG. 4.

As illustrated in FIGS. 1-8, at least a portion of the needle body 130 is curved along the length of the needle body 130. In an approach, and as illustrated in FIGS. 1-9, the entire length of the needle body 130 may be curved. As illustrated with reference to FIGS. 1 and 5, the slit 150 may be formed on the inside of the curvature of the needle body 130. For example, the slit 150 may be formed on the top part of the needle body 130 when the needle body 130 is arranged as illustrated in FIG. 5.

However, the present subject matter is not limited to this configuration. For example, when desired, the slit 150 may also be formed on the bottom part of the needle body 130, when the needle body 130 is arranged as illustrated in FIG. 5, or on either side of the needle body 130 (i.e., between the top and bottom sides of the needle body 130), when the needle body 130 is arranged as illustrated in FIG. 5.

When the entire length of the needle body 130 is curved, the curvature can be constant along the needle body 130, thereby forming a needle body that tracks along a circle of a predefined radius. The magnitude of the radius of curvature can be selected as needed. However, the needle body 130 can also be shaped to have a varied curvature throughout its length. For example, the needle body 130 can be shaped to track the outline of an ellipse or ovoid, with the dimensions selected as needed.

The suture thread 200 may be surgical thread. Therefore, the suture thread 200 may be made of material suitable for suturing bodily tissue. For example, the suture thread 200 may include natural materials, such as by way of non-limiting example, silk, and/or synthetic material, for example, polyester, polypropylene, nylon, etc.

The flexible member 300 connects the suture thread 200 to the needle body 130.

The flexible member 300 can be made of an elastomeric material. For example, the flexible member 300 can be made of a malleable elastomeric material. In a non-limiting example, the elastomeric material includes silicone. In another non-limiting example, the elastomeric material is made entirely of silicone, and may be malleable.

Figure 3:
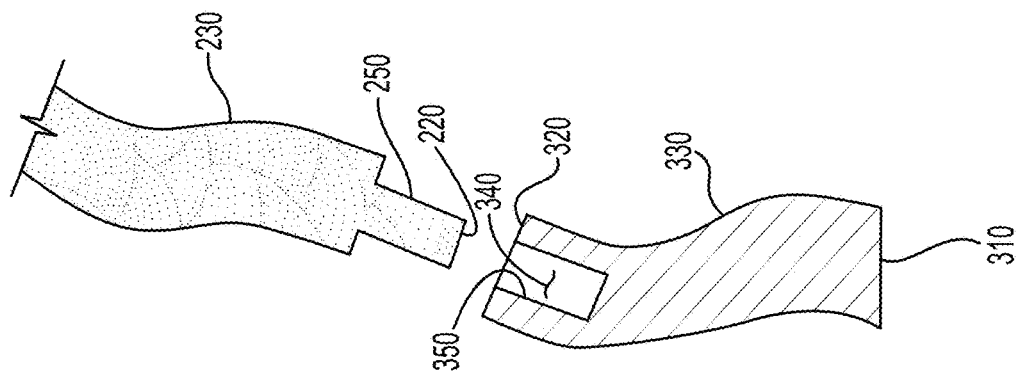
FIG. 3 is an exploded perspective view illustrating a flexible member and a suture thread of FIG. 2 in isolation from a needle body illustrated in FIG. 2.
Figure 2:
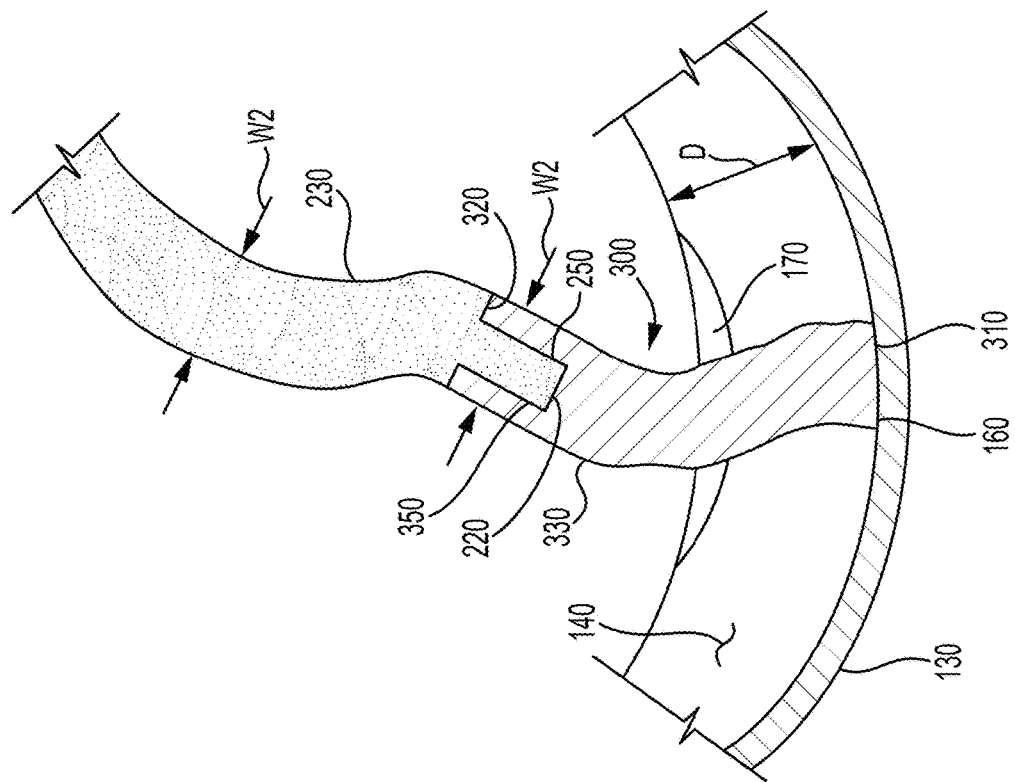
FIG. 2 is a magnified view of a region A of FIG. 1, illustrating a longitudinal cross-section of the portion of the suturing assembly included in region A.
Figure 4:
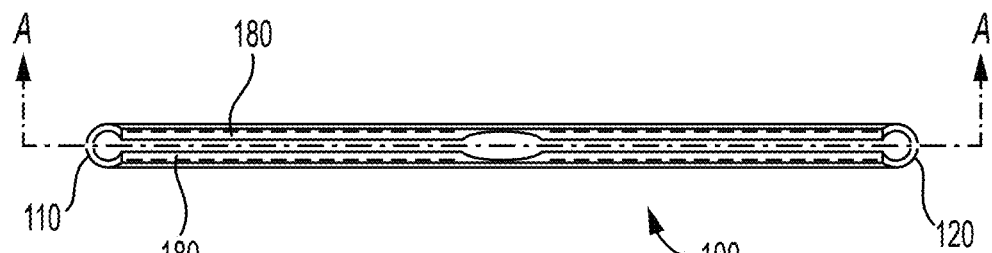
FIG. 4 is a top view illustrating the needle body of the suturing assembly of FIG. 1 in isolation from the flexible member and suture thread.

Referring to FIGS. 2-3, the flexible member 300 may include a first end 310, a second end 320, and a flexible member body 330 extending between the first and second ends 310, 320.

Referring to FIG. 2, the first end 310 of the flexible member 300 and/or a portion of the flexible member body 330 may be connected to an interior side surface 160 of the needle body 130 that defines the cavity 140.

For example, a side surface (e.g., an end side surface) defining the first end 310 of the flexible member 300 may be attached (e.g., adhered) to the interior side surface 160 of the needle body 130. Alternatively, or in addition, a portion of the flexible member body 330, proximate or adjacent to the first end 310, may be attached to the interior side surface 160 of the needle body 130.

An adhesive material, such as epoxy and/or other adhesives may be used to attach the end 310 side surface of the flexible member 300 and/or the portion of the flexible member body 330 to the interior side surface 160 of the needle body 130. For example, epoxy and/or other adhesives may be disposed between the interior side surface 160 and the end surface of the flexible member that defines the first end 310 of the flexible member 300. Alternatively, or in addition, epoxy and/or other adhesives may be disposed between the interior side surface 160 and the portion of the flexible member body 330 to which the interior side surface 160 is connected.

As illustrated with reference to FIGS. 2-3, the suture thread 200 may be connected to the flexible member body 330 and extend from the second end 320 of the flexible member body 330.

The connection between the suture thread 200 and the flexible member 300 may be made such that the flexible member 300 and the suture thread 200 form a substantially continuous thread, filament, string, line, etc., which may collectively be referred to as the "line". Notably, the continuous line is formed without tying a knot or creating a comparatively bulky connection scheme to connect the suture thread 200 and the flexible member 300 to one another. The continuous line connection taught by this specification avoids the formation of a localized bump or localized increase in diameter/width of the line that would otherwise result from a knot used in tying the flexible member 300 and the suture thread 200 to one another.

Figure 7:
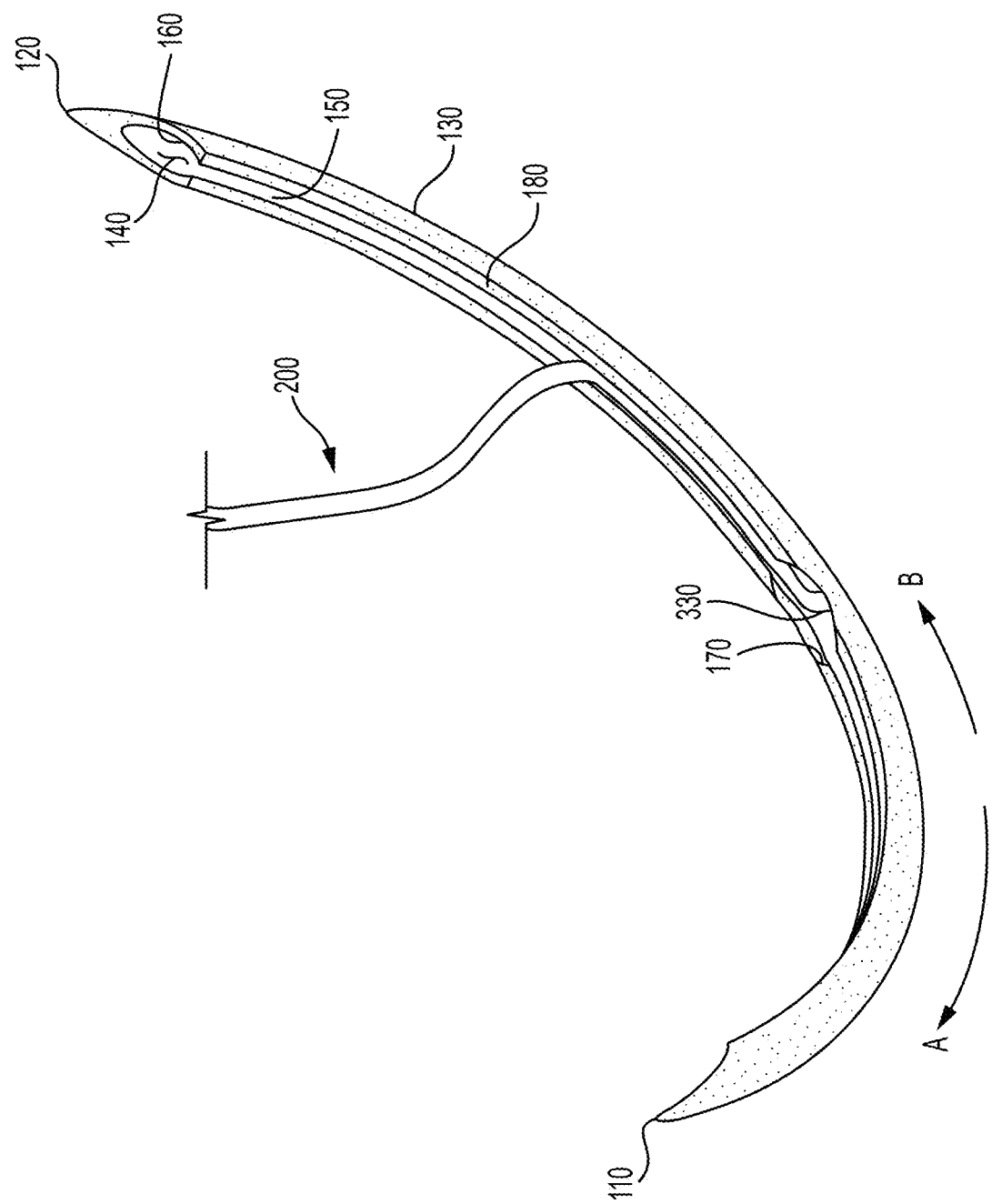
FIG. 7 is a perspective view illustrating the suturing assembly of FIG. 1 with the suture thread inserted in a cavity of the needle body along part of the way toward the right-hand-side tip of the needle body.
Figure 8:
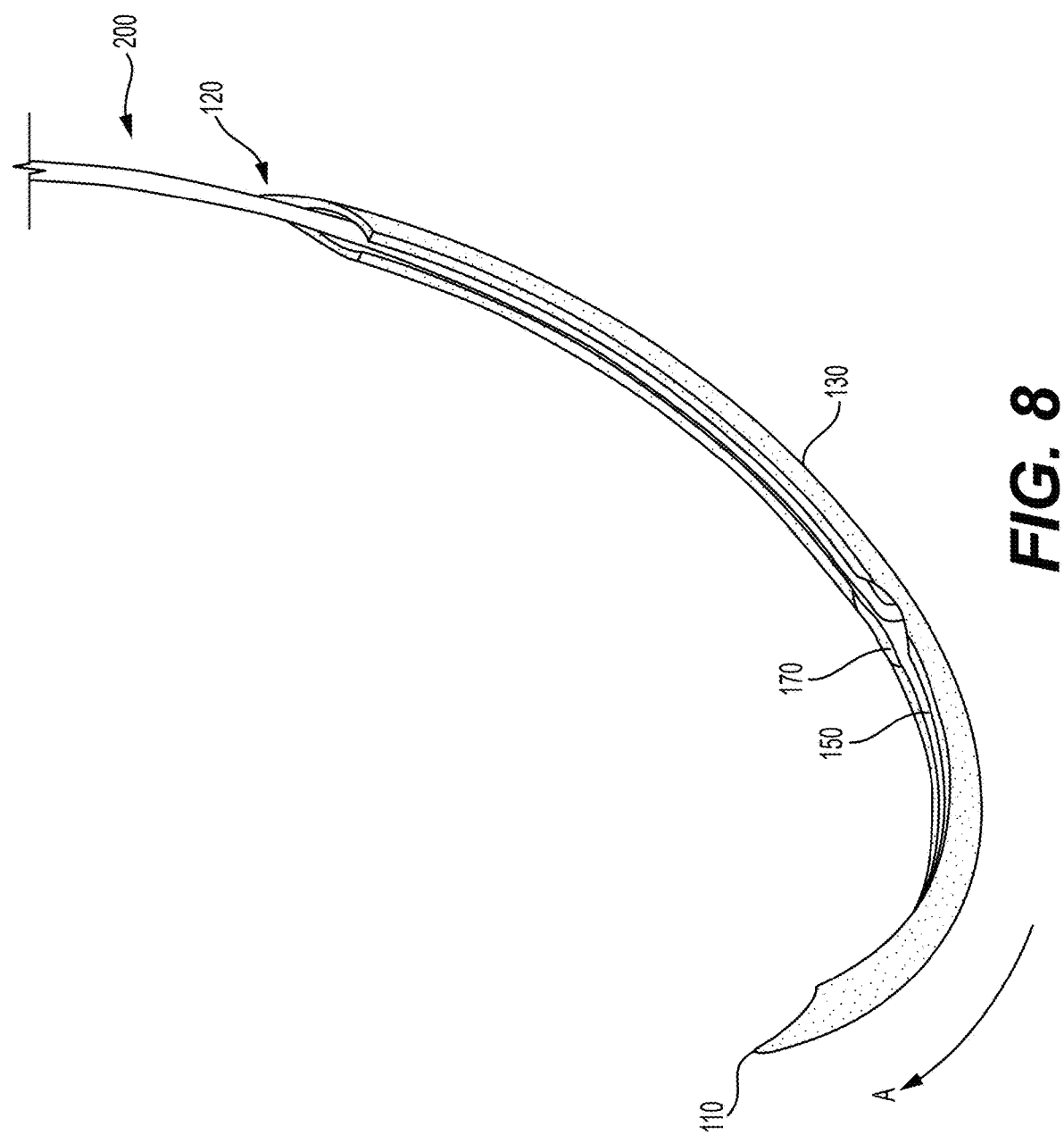
FIG. 8 is a perspective view illustrating the suturing assembly of FIG. 1 with the suture thread inserted in the cavity of the needle body along the entire way toward the right-hand-side tip of the needle body, and extending from the right-hand-side tip end of the needle body.
Figure 9:
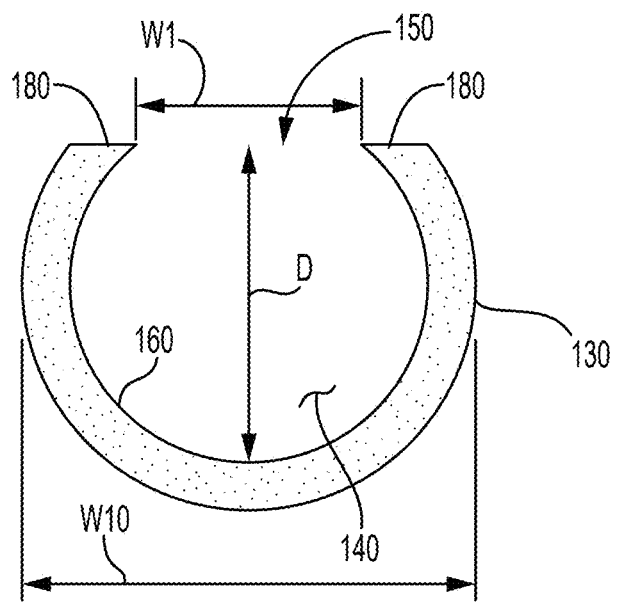
FIG. 9 is a cross-sectional view taken along line B-B of FIG. 5.

In addition, the flexible member 300 and a portion of the length of the suture thread 200 can be sized to fit in the cavity 140, as illustrated in FIGS. 7-8. Therefore, a width W1 of the slit 150 (see FIG. 1) can be substantially equal to or greater than a width/diameter W2 (see FIG. 2) of the flexible member 300 and/or of the suture thread 200. However, the suture thread 200 and the flexible member 300 need not have the same width/diameter as one another. For example, one selected from the group consisting of the suture thread 200 and the flexible member 300 may have a smaller width/diameter than the other, selected from the group consisting of the suture thread 200 and the flexible member 300, or a width that is greater than the other, selected from the group consisting of the suture thread 200 and the flexible member 300. Regardless of any size difference in width/diameter between the suture thread 200 and the flexible member 300, the width W1 of the slit 500 should be sized to enable the suture thread 200 and the flexible member 300 to pass therethrough.

Since the flexible member 300 and the suture thread 200 can be accommodated inside of the cavity 140, the needle 100 can avoid piercing a hole that is greater than the exterior diameter/width W10 (see FIG. 9) of the needle body 130 in the tissue of a patient when the suturing assembly of the present disclosure is used to suture a patient. Stated otherwise, the needle 100 can be passed through the tissue of a patient while having the flexible member 300 and the suture thread 200 inserted in the cavity 140 during the suturing process to pass the suture thread 200 from one side of the tissue to the other. Therefore, the size of the puncture created in the patient's tissue is limited to the size/width W10 of the needle body 130.

In use, the suture thread 200 can extend (continuously) from the rear end of the needle 100, as exemplarily illustrated in FIG. 8. In an example, and with reference to FIG. 8, the needle 100 can be rotated as illustrated by the curved arrow A, thereby turning the first end 110 into the penetrating end of the needle 100. Rotating the needle 100 along the curved path of the arrow A makes the second end 120 be the rear end of the needle 100 for this suture, with the suture thread 200 extending from the rear end 200, with the suture thread 200 and the flexible member 300 inserted in the cavity 140, between the point where the flexible member 300 is connected to the needle body 130 and the second end 120 of the needle 100.

FIG. 7 illustrates the suture thread 200 in the process of being inserted in the cavity 140, between the point where the flexible member 300 is connected to the needle body 130 and the second end 120 of the needle 100. For example, when starting in the configuration illustrated in FIG. 1, with the suture thread 200 and the flexible member 300 extending outwardly from the point where the flexible member 300 is connected to the interior side surface 160, FIG. 7 illustrates the flexible member 300 inserted in the cavity 140 and the suture thread 200 being inserted in about half of the length of the needle body 130 (relative to the point where the flexible member 300 is connected to the needle body 130 and the second end 120) toward the second end 120 thereof.

FIG. 8 illustrates the flexible member 300 and the suture thread 200 inserted in the cavity 140 along the entire way to the second end 120, with the suture thread 200 extending from the second end 120.

As illustrated in FIGS. 1 and 2, the flexible member 300 may be connected to the interior side surface 160 of the needle body 130 at about mid-length (or at approximately the center) of the needle body 130. However, the present disclosure is not limited to this configuration. For example, the flexible member 300 can be connected to different areas of the interior side surface 160 along the length of the needle body 130, whether to be disposed closer to the first end 110 than the second end 120, or vice-versa.

During a surgical procedure, when starting with the suturing assembly as illustrated in FIG. 1, and inserting the first end 110 of the needle 100 into the tissue of a patient in the rotational direction A, as illustrated in FIG. 7, at the time that about half of the length of the needle body 130 has been inserted in the tissue, the flexible member 300 makes contact with the constriction (or hole) in the tissue where the needle 100 has penetrated (when the flexible member 300 is connected to the interior side surface 160 at about mid-length of the of the needle body 130, as in the example illustrated in the drawings). When the needle body 130 is pushed into the tissue further (in the rotational direction A) the constriction (or hole opening) in the tissue guides the flexible member 300 toward the slit 150, and then inside of the cavity 140 through the slit 150. As the needle 100 is pushed into the tissue even further along the rotational direction A, the constriction (or hole opening) in the tissue guides the remainder of the flexible member 300 toward the slit 150 and into the cavity 140 through the slit 150. After the entire length of the flexible member 300 (which may be relatively short) is inserted in the cavity 140, the constriction (or hole opening in the tissue) guides the suture thread 200 toward the slit 150 and into the cavity 140 through the slit 150.

For example, FIG. 7 illustrates a stage (during surgery, for example) where about three-quarters of the needle body 130 has penetrated in tissue in the rotational direction A. FIG. 8 illustrates a stage (during surgery, for example) where the entire needle 100 has penetrated the patient's tissue in the rotational direction A, with the suture thread 200 extending from the second end 120 of the needle 100.

After the suture formed with reference to the process described in this specification with reference to FIGS. 7 and 8 has been completed (that is, when the needle 100 has penetrated the entire depth/thickness of the tissue in the rotational direction A and the suture thread 200 has been sufficiently tightened by the surgeon on the side of the tissue where the needle 100 exited), the needle 100, without needing reorientation of its piercing ends, can be used to form the subsequent suture by feeding the needle 100 in a rotational direction B, as shown in FIG. 7, opposite to the rotational direction A, to pierce the tissue with the second end 120.

Therefore, the configuration of the suturing assembly of the present subject matter eliminates the need to rotate a needle to have the sharp end of the needle face the tissue to be sutured, as must be performed when using conventional swaged needles. Therefore, the suturing assembly of the present subject matter can be used to increase the speed of suturing, reduce the overall surgery time, and reduce the post-surgery healing time by not requiring the surgeon to turn the needle body after each suture is completed to orient the sharp end of the needle toward the tissue that must be punctured to create the next suture.

The description of the usage of the suturing assembly above, with the first end 110 of the needle 100 penetrating the tissue first, is used merely to provide an example of how the suturing assembly of the present disclosure can be used. A surgeon or other medical professional can elect which end of the needle 100 to use first for penetrating the tissue since the needle 100 is bi-directional. Either the first end 110 or the second end 120 can be used to pierce the tissue first, with the flexible member 300 and the suture thread 200 being guided and inserted in the cavity 140 in the rear portion of the needle body 130 (rear relative to the insertion direction of the needle 100). That is, if the first end 110 of the needle 100 penetrates the tissue first, the second end 120 of the needle 100 is considered as the rear end. Similarly, if the second end 120 of the needle 100 penetrates the tissue first, the first end 110 of the needle 100 is considered as the rear end.

As illustrated in FIGS. 2 and 7-8, the needle body 130 may include a cutback 170 of the slit 150, adjacent to a location where the flexible member 300 is connected to the interior side surface 160 of the needle body 130. The cutback 170, as illustrated in FIGS. 2 and 7-8, increases the width W1 of the slit 150, thereby facilitating the insertion of the flexible member 300 (and the suture thread 200, depending on the length of the flexible member 300) in the cavity 140.

The connection between the flexible member 300 and the suture thread 200 will be described below.

Referring to FIG. 3, the suture thread 200 may include a first end 220 and a thread body 230 that extends from the first end 220 for a certain length.

The flexible member 300 may include a recess 340 extending in the flexible member body 330 from the second end 320. The recess 340 may define a sidewall 350 of the flexible member body 330.

The thread body 230 may include a mating portion 250 adjacent to the first end 220. As illustrated in FIG. 2, the mating portion 250 can be inserted (or disposed) in the recess 340 such that the mating portion 250 of the thread body 230 can contact the sidewall 350 of the flexible member body 330 inside of the recess 340. For example, the sidewall 350 can directly contact the mating portion 250 of the suture thread 200 in the recess 340.

The connection between the mating portion 250 of the thread body 230 and the sidewall 350 of the flexible member body 330 can be achieved by, for example, applying pressure and/or heat (e.g., thermocompression) to the flexible member 300 from the outside such that the flexible member 300, and more particularly, the sidewall 350 of the flexible member 300, can be pressed against the mating portion 240 of the suture thread 200.

The pressure and/or heat applied to the sidewall 350 can cause the sidewall 350 to be fused to (or to impregnate) the mating portion 250 of the thread body 230. The fusing of the sidewall 350 to the mating portion 250 of the suture thread 200 or the impregnation of the mating portion 250 of the thread 200 with the flexible material that makes up the sidewall 350 connects the suture thread 200 and the flexible member 300 to one another. The strength of the connection between the mating portion 250 of the suture thread 200 and the sidewall 350 of the flexible member 300 should be sufficiently strong to prevent disconnection between the flexible member 300 and the suture thread 200 during a surgical procedure (or during another type of a suturing operation, as the case may be).

Alternatively, or in addition, an adhesive may be applied to the sidewall 350 and the mating portion 250 (when these components are separated, as illustrated in FIG. 3) to connect the suture thread 200 and the flexible member 300 to one another. For example, epoxy can be disposed between the sidewall 350 of the flexible member 300 and the mating portion 250 of the suture thread 200.

FIG. 2 exemplarily illustrates the suture thread 200 and the flexible member 300 as having the same width/diameter W2. However, the present subject matter is not limited to this configuration. The suture thread 200 and the flexible member 300 can have different widths/diameters so long as the width or diameter of the suture thread 200 is equal to or smaller than the width W1 of the slit 150 and the width or diameter of the flexible member 300 is equal to or smaller than the width W1 of the slit 150. This configuration ensures that the flexible member 300 and the suture thread 200 can be: a) freely inserted in the cavity 140 along the length of the needle body 130 through the slit 150, and b) freely removed from the cavity 140 along the length of the needle body 130 through the slit 150.

FIGS. 2-3 illustrate that the mating portion 250 of the thread body 230 can have a reduced width as compared to the width W2 of the remainder of the thread body 230. This configuration can be used to provide a connection of a uniform width/diameter between the suture thread 200 and the flexible member 300, as exemplarily illustrated in FIG. 2. However, the present subject matter is not limited to this configuration.

Figure 10:
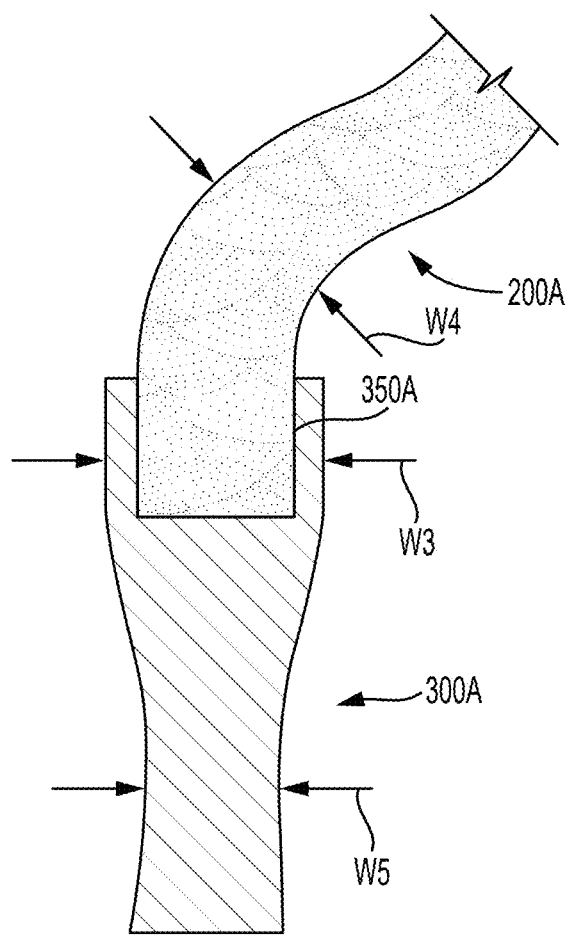
FIG. 10 is a cross-sectional view illustrating a flexible member and a suture thread connected to one another according to an exemplary embodiment of the present disclosure.

In an alternate configuration, as illustrated in FIG. 10, a suture thread 200A may have a substantially uniform diameter/width W4 throughout. A flexible member 300A may have a variable diameter/width W5 throughout its length. A sidewall 350A of the flexible member 300A may extend on the suture thread 200, over a certain distance adjacent to an end portion of the suture thread 200A, to connect the suture thread 200A with the flexible member 300A, as described in this specification with reference to the flexible member 300 and the suture thread 200. However, a width/diameter W3 of the flexible member 300A at the connection between the flexible member 300A and the suture thread 200A may be greater than the width/diameter W4 of the suture thread 200A and/or greater than the width/diameter W5 at other portions of the flexible member 300A. This configuration is permissible so long as the width or diameter W3 of the flexible member 300A is equal to or smaller than the width W1 of the slit 150.

The flexible member 300, 300A and the suture thread 200, 200A may be sized to fit entirely in the cavity 140. For example, and with reference to FIG. 2, a depth D of the cavity 140 may be sized to be equal to or greater than the widths W2, W3, W4 and W5 as taught by this specification. This configuration prevents the flexible member 300, 300A and the suture thread 200, 200A from protruding outside of cavity 140 during a surgical procedure, thereby ensuring that the width/diameter of the puncture in the patient's body does not exceed the width/diameter of the needle body 130.

Therefore the widths W2, W3, W4 and W5 may be smaller than, or at most, substantially equal to the width W1 of the slit 150 (such that the flexible member 300, 300A and the suture thread 200, 200A can fit through the slit 150), and the widths W2, W3, W4 and W5 may be smaller than or equal to the depth D of the cavity 140.

However, when the needle body 130 may have a longitudinal portion (or strip) thereof removed, the removal of the longitudinal portion of the body 130 may form the surfaces 180 on the needle body 130 (see FIGS. 1 and 9), said surfaces 180 extending adjacent to the slit 150 along the length of the needle body 130. Since the removal of the longitudinal body portion (to form the surfaces 180) reduces the overall external diameter/width of the needle body 100 (in the top-bottom direction, when the needle 100 is oriented as shown in FIG. 5), a slight protrusion of the flexible member 300, 300A and/or the suture thread 200, 200A (including a protrusion caused by the width W3 as described in this specification) over the border of the surfaces 180 (e.g., above the slit 150) merely "fills back" the removed material from the needle body 130, and therefore, it does not increase the overall external diameter/width of the needle body 100.

Stated otherwise, so long as the amount by which the flexible member 300, 300A and/or the suture thread 200, 200A protrudes above the slit 150 (including a protrusion caused by the width W3 as described in this specification) does not exceed the depth of material that was removed from the needle body 130 to create the surfaces 180, the needle body 130 with the flexible member 300, 300A and/or the suture thread 200, 200A will not increase the overall external diameter/width of the needle body 130. As such, the suturing assembly of the present subject matter can be used without increasing the puncture hole in a patient's body beyond the overall external diameter/width of the needle body 130.

While the suturing assembly of the present subject matter is described as being used in surgical applications on humans, the use of said suturing assembly is not limited to surgery and is not limited to use on humans. For example, a suturing assembly as described in this specification can be used for surgical procedures in animals. In addition, a suturing assembly as described in this specification can be used in any other non-surgical application where the use of a curved double-headed needle can facilitate the sewing/stitching process while reducing the damage done to the material being punctured by limiting the size of the puncture holes to the size of the needle.

A method of suturing includes obtaining a suturing assembly as described in this specification.

The method of suturing then includes moving the needle body along a first movement path to puncture tissue or material being sutured with the first end of the needle, the moving of the needle along the first movement path causes the needle to: a) pierce a first side surface of the tissue or material being sutured with the first end of the needle, b) pass through the tissue or material being sutured, and c) exit from a second side surface of the material being sutured.

In addition, the method of suturing includes: moving the needle body along a second movement path, different from the first movement path (e.g., opposite to the first movement path), to puncture the tissue or material being sutured with the second end of the needle, the moving of the needle along the second movement path causes the needle to: a) pierce the second side surface of the tissue or material being sutured with the second end of the needle, b) pass through the tissue or material being sutured, and c) exit from the first side surface of the material being sutured.

Further, the method of suturing can include sequentially repeating the moving of the needle body along the first movement path and the second movement path until the suturing has been completed.

While the present disclosure has been particularly shown and described with reference to exemplary embodiments thereof, it will be apparent to those of ordinary skill in the art that various changes in form and detail may be made therein without departing from the spirit and scope of the present disclosure as defined by the following claims.

What is claimed is:

1. A suturing assembly, comprising:
    a needle, the needle having:
        a first end defining a first tip of the needle;
        a second end defining a second tip of the needle, and
        a needle body extending between said first and second ends, the needle body including:
            a cavity that extends throughout the needle body, along a length of the needle body, between said first and second ends, and
            a slit extending along the length of the needle body, between said first and second ends, the slit exposing the cavity of the needle body to an outside of the needle body along the length of the needle body, wherein at least a portion of the needle body is curved along the length of the needle body;
    a suture thread; and
    a flexible member, said flexible member having:
        a first end;
        a second end; and
        a flexible member body extending between the first and second ends of the flexible member,
    wherein the first end of the flexible member or a portion of the flexible member body is connected to an interior side surface of the needle body that defines the cavity,
    wherein the suture thread is connected to the flexible member body and extends from the second end of the flexible member body, and
    wherein the needle body includes a cutback of the slit adjacent to a location where the first end of the flexible member or the portion of the flexible member body is connected to the interior side surface of the needle body, the cutback increasing a width of the slit.

2. The suturing assembly of claim 1, wherein a width or diameter of the suture thread is equal to or smaller than a width of the slit of the needle body such that the suture thread can be: a) insertable in the cavity along the length of the needle body through the slit, or b) removable from the cavity along the length of the needle body through the slit.

3. The suturing assembly of claim 1, wherein a width or diameter of the flexible member body is equal to or smaller than a width of the slit of the needle body such that the flexible member body can be passed through the slit.

4. The suturing assembly of claim 1, wherein the flexible member body comprises silicone.

5. The suturing assembly of claim 1, wherein the needle body is curved along its entire length.

6. The suturing assembly of claim 1, further comprising an adhesive material disposed between the interior side surface of the needle body that defines the cavity and an end surface of the flexible member, said end surface of the flexible member defining the first end of the flexible member.

7. The suturing assembly of claim 1, further comprising an adhesive material disposed between the interior side surface of the needle body that defines the cavity and the portion of the flexible member body that is connected to said interior side surface.

8. The suturing assembly of claim 1, wherein the first end of the flexible member or the portion of the flexible member body is connected to the interior side surface of the needle body that defines the cavity at mid-length of the needle body.

9. The suturing assembly of claim 1, wherein the first end of the flexible member or the portion of the flexible member body is connected to the interior side surface of the needle body that defines the cavity at a portion of the needle body that is located closer to the first end of the needle than the second end of the needle.

10. The suturing assembly of claim 1, wherein the flexible member includes a recess extending in the flexible member body from the second end of the flexible member body, the recess defining a sidewall of the flexible member body.

11. The suturing assembly of claim 10, wherein the suture thread includes a mating portion adjacent to a first end of the suture thread, wherein the mating portion of the suture thread is disposed in the recess of the flexible member.

12. The suturing assembly of claim 11, wherein a sidewall of the flexible member, defined by the recess thereof, is fused to the mating portion of the suture thread.

13. The suturing assembly of claim 11, further comprising an adhesive material disposed between a sidewall of the flexible member, defined by the recess thereof, and the mating portion of the suture thread.

14. The suturing assembly of claim 11, wherein the suture thread has a smaller width or diameter at the mating portion thereof than at a portion thereof that excludes the mating portion.

15. The suturing assembly of claim 11, wherein the suture thread has a uniform width or diameter throughout its length.

16. The suturing assembly of claim 1, wherein the cavity extends throughout an entire length of the needle body.

17. The suturing assembly of claim 1, wherein the slit extends along an entire length of the needle body.

18. A method of suturing, comprising:
    obtaining a suturing assembly, said suturing assembly including:
        a needle, the needle having:
            a first end defining a first tip of the needle;
            a second end defining a second tip of the needle, and
            a needle body extending between said first and second ends, the needle body including:
                a cavity that extends throughout the needle body, along a length of the needle body, between said first and second ends, and
                a slit extending along the length of the needle body, between said first and second ends, the slit exposing the cavity of the needle body to an outside of the needle body along the length of the needle body, wherein at least a portion of the needle body is curved along the length of the needle body;
        a suture thread; and
        a flexible member, said flexible member having:
            a first end;
            a second end; and
            a flexible member body extending between the first and second ends of the flexible member,
        wherein the first end of the flexible member or a portion of the flexible member body is connected to an interior side surface of the needle body that defines the cavity,
        wherein the suture thread is connected to the flexible member body and extends from the second end of the flexible member body, and wherein the needle body includes a cutback of the slit adjacent to a location where the first end of the flexible member or the portion of the flexible member body is connected to the interior side surface of the needle body, the cutback increasing a width of the slit;

moving the needle body along a first movement path to puncture tissue or material being sutured with the first end of the needle, the moving of the needle along the first movement path causes the needle to: a) pierce a first side surface of the tissue or material being sutured with the first end of the needle, b) pass through the tissue or material being sutured, and c) exit from a second side surface of the material being sutured; and moving the needle body along a second movement path, different from the first movement path, to puncture the tissue or material being sutured with the second end of the needle, the moving of the needle along the second movement path causes the needle to: a) pierce the second side surface of the tissue or material being sutured with the second end of the needle, b) pass through the tissue or material being sutured, and c) exit from the first side surface of the material being sutured.

19. The method of suturing of claim 18, wherein the steps of moving the needle body along the first movement path and the second movement path are sequentially repeated until the suturing has been completed.

* * * * *